US009095652B2

(12) United States Patent
Dewey (10) Patent No.: US 9,095,652 B2
(45) Date of Patent: *Aug. 4, 2015

(54) SYSTEM AND METHOD FOR CONTROLLING ADMINISTRATION OF MEDICAL FLUID

(75) Inventor: Paul Dewey, Poway, CA (US)

(73) Assignee: CareFusion 303, Inc., San Diego, CA (US)

( * ) Notice: Subject to any disclaimer, the term of this patent is extended or adjusted under 35 U.S.C. 154(b) by 428 days.

This patent is subject to a terminal disclaimer.

(21) Appl. No.: 13/481,609

(22) Filed: May 25, 2012

(65) Prior Publication Data

US 2012/0238997 A1 Sep. 20, 2012

Related U.S. Application Data

(63) Continuation of application No. 11/414,794, filed on May 1, 2006, now Pat. No. 8,211,054.

(51) Int. Cl.
*A61M 31/00* (2006.01)
*A61M 5/168* (2006.01)
(Continued)

(52) U.S. Cl.
CPC ....... *A61M 5/16881* (2013.01); *A61M 5/14216* (2013.01); *A61M 5/16809* (2013.01);
(Continued)

(58) Field of Classification Search
CPC ............... A61M 5/14216; A61M 5/14224; A61M 5/16813; A61M 5/16881; A61M 5/16886; A61M 2205/3592; A61M 2205/0288; A61M 2205/0294; A61M 2205/3306; A61M 2205/3561; A61M 5/172
USPC ............... 604/65–67, 131, 132, 151, 153
See application file for complete search history.

(56) References Cited

U.S. PATENT DOCUMENTS

| | | |
|---|---|---|
| 3,990,443 A | 11/1976 | Fletcher |
| 4,121,584 A | 10/1978 | Turner et al. |

(Continued)

FOREIGN PATENT DOCUMENTS

| | | |
|---|---|---|
| DE | 19501691 | 7/1995 |
| JP | H09502245 | 4/1997 |

(Continued)

OTHER PUBLICATIONS

International Preliminary Report on Patentability PCT/US2007/067665 issued Nov. 4, 2008.

(Continued)

*Primary Examiner* — Theodore Stigell
(74) *Attorney, Agent, or Firm* — McDermott Will & Emery LLP (57) ABSTRACT

A system for controlling administration of medical fluid includes a fluid passageway to which is attached a first flow regulator, a second flow regulator, and a flow detector. The system also includes a controller for controlling the first and second flow regulators in response to a measurement taken by the flow detector of fluid movement in the fluid passageway. The first flow regulator, such as a pump, is configured to maintain fluid movement at flow values greater than an unrestricted flow value. The second flow regulator, such as a variable adjustable valve, is configured to maintain fluid movement at a flow value less than the unrestricted flow value. A method of controlling administration of medical fluid includes obtaining a target flow value, moving fluid through the disposable assembly, taking a measurement of fluid movement in the disposable assembly, and actuating a flow regulating apparatus.

20 Claims, 8 Drawing Sheets

(51) Int. Cl.
*A61M 5/142* (2006.01)
*A61M 5/172* (2006.01)

(52) U.S. Cl.
CPC ....... *A61M5/16813* (2013.01); *A61M 5/16886* (2013.01); *A61M 5/172* (2013.01); *A61M 2205/0288* (2013.01); *A61M 2205/0294* (2013.01); *A61M 2205/3306* (2013.01); *A61M 2205/3561* (2013.01); *A61M 2205/3592* (2013.01)

(56) References Cited

U.S. PATENT DOCUMENTS

| | | | |
|---|---|---|---|
| 4,261,356 A | 4/1981 | Turner et al. | |
| 4,321,461 A | 3/1982 | Walter, Jr. et al. | |
| 4,411,651 A | 10/1983 | Schulman | |
| 4,447,224 A | 5/1984 | DeCant, Jr. et al. | |
| 4,670,007 A | 6/1987 | Wheeldon et al. | |
| 4,725,269 A | 2/1988 | Danby et al. | |
| 4,838,856 A | 6/1989 | Mulreany et al. | |
| 5,154,704 A | 10/1992 | Archibald | |
| 5,163,909 A | 11/1992 | Stewart | |
| 5,211,626 A | 5/1993 | Frank et al. | |
| 5,584,811 A | 12/1996 | Ross et al. | |
| 5,743,878 A | 4/1998 | Ross et al. | |
| 5,904,666 A | 5/1999 | DeDecker et al. | |
| 6,053,887 A | 4/2000 | Levitas et al. | |
| 6,120,475 A | 9/2000 | Chen | |
| 6,280,148 B1 | 8/2001 | Zengerle et al. | |
| 6,287,294 B1 | 9/2001 | Lemelson | |
| 6,375,638 B2 | 4/2002 | Nason et al. | |
| 6,386,050 B1 * | 5/2002 | Yin et al. | 73/861.95 |
| 6,413,238 B1 * | 7/2002 | Maget | 604/132 |
| 6,416,293 B1 | 7/2002 | Bouchard et al. | |
| 6,475,180 B2 | 11/2002 | Peterson et al. | |
| 6,530,286 B1 | 3/2003 | Carver et al. | |
| 6,558,346 B1 | 5/2003 | Yoshioka et al. | |
| 6,659,980 B2 | 12/2003 | Moberg et al. | |
| 6,685,668 B1 | 2/2004 | Cho et al. | |
| 6,768,425 B2 * | 7/2004 | Flaherty et al. | 340/870.07 |
| 6,812,624 B1 | 11/2004 | Pei et al. | |
| 6,940,211 B2 | 9/2005 | Pelrine et al. | |
| 7,064,472 B2 | 6/2006 | Pelrine et al. | |
| 8,211,054 B2 * | 7/2012 | Dewey | 604/67 |
| 2003/0040722 A1 | 2/2003 | Massengale et al. | |
| 2003/0130625 A1 | 7/2003 | Jacobson et al. | |
| 2004/0008853 A1 * | 1/2004 | Pelrine et al. | 381/191 |
| 2006/0004330 A1 * | 1/2006 | Carlisle et al. | 604/246 |

FOREIGN PATENT DOCUMENTS

| | | |
|---|---|---|
| JP | 2002126092 | 5/2002 |
| JP | 2004533856 | 11/2004 |
| JP | 2005514175 | 5/2005 |
| RU | 2262081 | 10/2005 |
| WO | WO 91/09636 | 7/1991 |
| WO | WO 01/43798 | 6/2001 |
| WO | WO 03/075984 | 9/2003 |
| WO | WO 2005/097235 | 10/2005 |

OTHER PUBLICATIONS

International Search Report PCT/US2007/067665 mailed Sep. 4, 2007.
Office Action dated Dec. 6, 2010, from related Russian Application No. 2008147087.
Schnell et al., "Ein thermischer Durchflußsensor für die Infusionstechnik a Thermal Flow Sensor for Infusion Systems," Biomedizinesche Technik, Flachverlag Schiele Und Schoen GmbH., Berlin, DE, vol. 40, No. 3, pp. 50-53 (XP000491947, ISSN: 0013-5585), Mar. 1995 (Abstract).

* cited by examiner

SYSTEM AND METHOD FOR CONTROLLING ADMINISTRATION OF MEDICAL FLUID

CROSS REFERENCE TO RELATED APPLICATIONS

The present application is a continuation of U.S. application Ser. No. 11/414,794, U.S. Pat. No. 8,211,054, and filed May 1, 2006, which is incorporated herein by reference.

BACKGROUND OF THE INVENTION

1. Field of the Invention

The invention relates generally to the controlled administration of medical fluid and, more particularly, to intravenous fluid delivery implementing a control loop to achieve and automatically maintain a desired delivery parameter.

2. Description of the Related Art

Intravenous ("IV") fluid delivery systems are used to deliver medical fluid to patients at controlled rates. Many such IV fluid delivery systems exist and in one case, precise infusion pumps have been developed to more accurately provide medical fluids to patients in accordance with physician prescriptions. In most cases, an open-loop pump control system is used in which a processor varies the speed of a fluid pump based on a predefined function of various parameters, such as fluid type, infusion profile, and programmed flow rate. Such processor-controlled, open-loop pump systems can be expensive and are usually complex in that they are highly engineered with close tolerance parts to produce the desired accuracy of fluid delivery.

In most cases, such open-loop pumps do not use any feedback to alter the control over the pumping mechanism. Sensors in the pump or associated with the fluid delivery are usually used to detect alarm conditions associated with peripheral events, such as an excessive amount of air in the fluid delivery line, occlusion of the fluid tubing above or below the pump, and depletion of medical fluid in the container. The highly engineered pumping mechanism and processor control accounts for almost the entire accuracy of the pump. However, the rate of fluid delivery is also affected by the precision of disposable components, such as the tubing, used in the fluid path that conveys the medical fluid to a patient. Variations in the internal diameter and material hardness of tubing and pumping components comprising the disposable components cannot be readily compensated in an open-loop control algorithm since such variations may change with the age of the component and since it is impractical to measure such variations directly. As a result, disposable components subject to tight tolerance specifications must be used in such open-loop systems to ensure accuracy of fluid delivery. The tight tolerance specifications increase manufacturing costs which are ultimately borne by the patient.

Certain closed-loop systems have been disclosed in the art over the years and seek to maintain or increase medical fluid delivery accuracy. In a closed-loop system, a parameter or parameters associated with the fluid delivery process are measured to control the fluid delivery system. Prior closed-loop systems have often determined the flow rate of medical fluid to the patient by indirect means, such as by measuring internal pressure forces on the wall of a fluid passageway or by measuring a fluid pressure gradient across a constriction in the fluid passageway. Some prior systems have attempted to measure actual movement of the fluid in the fluid passageway; however, some such systems were invasive in that they involved physical contact with the medicinal fluid and were not implemented. Others required sensors and processing systems that were expensive and also were not implemented.

Fluid delivery manufacturers strive to provide a high level of fluid delivery accuracy while at the same time strive to control costs to patients. A closed-loop pump system and method could provide useful information about the actual delivery of fluid to the patient and if accurate enough, the pump device itself and disposable administration components could be manufactured with looser tolerances thereby reducing costs to the patient. Such accuracy would enable manufacturers to provide different means for delivering medical fluids to patients, including a reliance, at least partially, on gravity as the force to cause the fluid to flow to the patient.

Hence, those skilled in the art have recognized a need for a more advanced medical fluid delivery system and method using a sensor or sensors that measure actual fluid flow to the patient and use such sensed flow information to regulate the fluid delivery. Those skilled in the art have also noted a need for a lower cost fluid delivery apparatus, including a flow regulator and flow conduits, having looser tolerances on parts so that costs are more controlled. Accordingly, it is desirable to provide a lower cost, less complex system for delivery of medical fluids that reduces costs yet provides accuracy in fluid delivery. The present invention satisfies these and other needs.

SUMMARY OF THE INVENTION

Briefly and in general terms, the present invention is directed to a system and method for providing accurate medical fluid delivery to a patient using flow regulators and a flow sensor to determine the actual flow of the medical fluid to the patient so as to allow for control the flow regulators.

In an aspect of the present invention, a fluid control system for controlling administration of fluid from a medicament container comprises a fluid passageway comprising an inlet, an outlet, and an internal volume through which unrestricted movement of fluid corresponds to an unrestricted flow value, a first flow regulator attached to the fluid passageway and configured to keep fluid movement in the fluid passageway at a flow value greater than the unrestricted flow value, a second flow regulator attached to the fluid passageway and configured to keep the fluid movement in the fluid passageway at a flow value less than the unrestricted flow value, a flow detector attached to the fluid passageway and configured take a measurement of the fluid movement in the fluid passageway, and a controller removably attached to the fluid passageway and coupled to the flow detector, the first flow regulator, and the second flow regulator, the controller configured to control the first and second flow regulators in response to the measurement by the flow detector.

The first flow regulator in detailed aspects of the invention comprises a pump chamber having a moveable wall coupled to a pump driver, the pump chamber disposed in the fluid passageway and configured for one-way fluid flow in a direction from the inlet to the outlet of the fluid passageway, the pump driver comprising an elastomeric dielectric film having a first side and a second side, the first side coated with a first expandable conductive film connected to a first electrode, the second side coated with a second expandable conductive film connected to a second electrode, the dielectric film configured to expand in response to a voltage applied to the first and second electrodes.

The second flow regulator in detailed aspects of the invention is further configured to keep the fluid movement in the fluid passageway at a flow value equal to the unrestricted flow value. In yet other detailed aspects, the second flow regulator comprises a variably adjustable valve configured to restrict the fluid movement in the fluid passageway.

The flow detector in detailed aspects of the invention comprises a heat source disposed outside the internal volume of the fluid passageway and adapted to heat fluid located at a heating region in the fluid passageway, a light source disposed outside the internal volume of the fluid passageway and adapted to produce an interrogating light directed toward fluid located at an interrogating region in the fluid passageway, a light detector disposed outside the internal volume of the fluid passageway and adapted to detect optical characteristics of the fluid in the interrogating region, and to detect changes in the optical characteristics when the heated fluid from the heating region enters the interrogating region.

In another aspect of the present invention, a method of controlling administration of fluid from a medicament container comprises obtaining a target flow value, moving fluid through a disposable assembly comprising a fluid passageway and a flow regulating apparatus, the fluid passageway comprising an inlet, an outlet, and an internal volume through which unrestricted movement of the fluid corresponds to an unrestricted flow value, the flow regulating apparatus comprising a first flow regulator and a second flow regulator, taking a measurement of fluid movement in the fluid passageway, and actuating the flow regulating apparatus when the fluid movement does not correspond to the target flow value, including changing the operational status of the second flow regulator when the target flow value is less than the unrestricted flow value, and changing the operational status of the first flow regulator when the target flow value is greater than the unrestricted flow value.

Actuating the flow regulating apparatus, in detailed aspects of the invention, includes changing the operational status of the second flow regulator when the target flow value is equal to the unrestricted flow value. In other detailed aspects, actuating the flow regulating apparatus comprises actuating the flow regulating apparatus when there is a change in the amount of fluid in the medicament container or a change in elevation of the medicament container relative to an outlet of an administration tube extending from the outlet of the fluid passageway. In yet other detailed aspects, actuating the flow regulating apparatus comprises applying a voltage to a first electrode and a second electrode, the first electrode connected to a first expandable conductive coating on a first side of an elastomeric dielectric film, the second electrode connected to a second expandable conductive coating on a second side of the elastomeric dielectric film, the elastomeric dielectric film coupled to a moveable wall disposed on the fluid passageway and configured to expand in response to the applied voltage.

Taking a measurement of fluid movement in the fluid passageway, in other detailed aspects, comprises heating fluid in a heating region in the fluid passageway, the fluid heated with a heat source disposed outside the internal volume of the fluid passageway, illuminating fluid in an interrogating region in the fluid passageway, the fluid illuminated with a light source disposed outside the internal volume of the fluid passageway, detecting optical characteristics of the fluid in the interrogating region, the optical characteristics detected with a light detector disposed outside the internal volume of the fluid passageway, and detecting changes in the optical characteristics, the changes detected with the light detector.

In another aspect of the present invention, a fluid control system for controlling administration of fluid from a medicament container comprises a primary fluid inlet, a pump chamber in fluid communication with the primary fluid inlet, the pump chamber comprising a moveable wall and a pump outlet, the pump chamber configured for one-way fluid flow from the primary fluid inlet to the pump chamber and for one-way fluid flow from the pump chamber to the pump outlet, a pump driver coupled to the moveable wall of the pump chamber and configured to move the moveable wall in response to a pump signal, a flow restrictor in fluid communication with the pump outlet, the flow restrictor comprising a restrictor outlet and configured to selectively increase and decrease fluid flow through the restrictor outlet, a restrictor driver connected to the flow restrictor and configured to actuate the flow restrictor device in response to a restrictor signal, a flow detector comprising a fluid conduit disposed between the flow restrictor and the pump chamber, the flow detector configured to produce and detect a thermal change in fluid in the fluid conduit and to provide a detector signal representative of an existing fluid flow rate in the fluid conduit, a user input device configured to obtain a target flow rate from a user, and a controller in communication with the pump driver, the restrictor driver, and the flow detector, the controller configured to produce the pump signal and the restrictor signal to adjust the existing fluid flow rate to the target fluid flow rate and to automatically maintain the existing flow rate at the target fluid flow rate.

In detailed aspects of the invention, the fluid control system comprises a disposable assembly and a reusable assembly attached to the disposable assembly, the reusable assembly configured to be detached from the disposable assembly, the reusable assembly comprising the controller and the user input device, a display configured to communicate a flow rate, and a power source, the disposable assembly comprising the primary fluid inlet, the pump chamber, the pump driver, the flow restrictor, the restrictor driver, and the flow detector.

The flow restrictor in detailed aspects of the invention comprises a manual adjustment device connected to the flow restrictor device, the manual adjustment device sized to be manipulated by the user and configured to change movement of fluid through the restrictor outlet.

The pump driver in detailed aspects of the invention comprises a first diaphragm comprising a first elastomeric dielectric film disposed between a first pair of expandable conductive coatings and a second diaphragm comprising a second elastomeric dielectric film disposed between a second pair of expandable conductive coatings, the first and second diaphragms coupled to the moveable wall of the pump chamber, the first diaphragm configured to move the moveable wall in a first direction in response to voltage applied to the first pair of coatings, the second diaphragm configured to move the moveable wall in a second direction in response to voltage applied to the second pair of coatings. In other detailed aspects, the pump driver comprises a piezoelectric device coupled to the moveable wall of the pump chamber, the piezoelectric device configured to move the moveable wall in response to a voltage applied to the piezoelectric device.

The detector signal from the flow detector, in detailed aspects of the invention, represents a time period in which the thermal change travels a predetermined distance in the fluid conduit of the flow detector.

The flow detector in detailed aspects of the invention comprises a heat source disposed outside an internal volume of the fluid conduit of the flow detector, the heat source adapted to heat fluid in a heating region in the fluid conduit, a light source disposed outside the internal volume and adapted to produce an interrogating light directed toward fluid in an interrogating region in the fluid conduit, a light detector disposed outside the internal volume and adapted to detect optical characteristics of the fluid in the interrogating region, and to detect changes in the optical characteristics when the heated fluid from the heating region enters the interrogating region. In more detailed aspects, the heat source is an optical device.

The features and advantages of the invention will be more readily understood from the following detailed description which should be read in conjunction with the accompanying drawings.

DETAILED DESCRIPTION OF THE PREFERRED EMBODIMENTS

Figure 1:
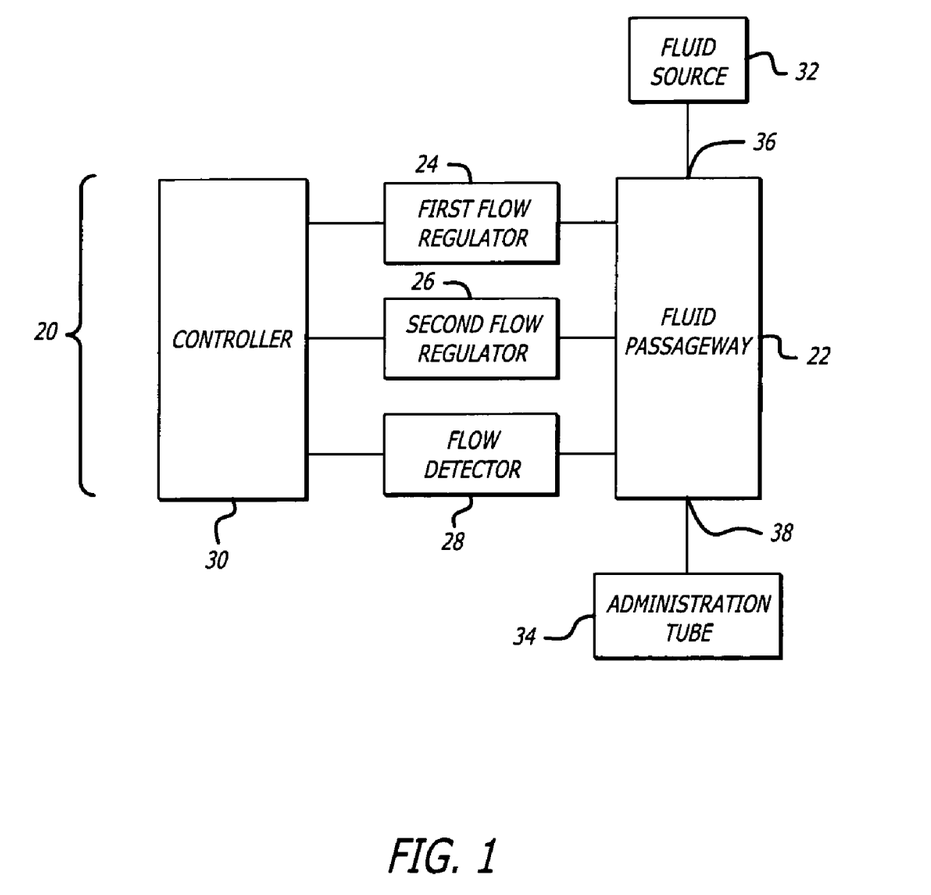
FIG. 1 is a block diagram of a system for controlling the administration of fluid showing a fluid passageway to which is connected a fluid source, a first flow regulator, a second flow regulator, a flow detector, and a fluid administration tube, wherein the first and second flow regulators and the flow detector being in communication with a controller.

Referring now in more detail to the exemplary drawings for purposes of illustrating embodiments of the invention, wherein like reference numerals designate corresponding or like elements among the several views, there is shown in FIG. 1 a block diagram of a system 20 for controlling administration of fluid from a medicament container or fluid source. The system includes a fluid passageway 22 through which fluid flows. Attached to the fluid passageway is a first flow regulator 24, a second flow regulator 26, and a flow detector 28. As will be described in greater detail below, the flow detector 28 is configured to take a measurement of actual fluid movement in the fluid passageway. Removably attached to the fluid passageway is a controller 30 configured to control the first and second flow regulators in response to the measurement by the flow detector.

The fluid passageway 22 has an inlet 36 to which a fluid source 32 may be connected and an outlet 38 to which an administration tube 34 may be connected or at which an administration tube forms a part. One example of a suitable fluid source is an intravenous (IV) bag that contains a medical fluid. When the system 20 is in use, the administration tube 34 is connected to a patient intended to receive the medical fluid. The fluid passageway 22 has an internal volume configured to allow movement of fluid therethrough. Fluid movement may be restricted by a valve or other adjustable device attached to the fluid passageway. Unrestricted fluid movement through the internal volume of the passageway corresponds to an unrestricted flow value. For example, when a valve or other adjustable device attached to the fluid passageway is in a fully open position, gravity induces fluid movement so that a volume of fluid flow exits the outlet 38 of the fluid passageway over a period of time. In this case, the unrestricted flow value may be represented by a flow rate in terms of milliliters per hour (ml/hr). It will be appreciated that the flow value may be represented in other terms, such as mass and weight.

Still referring to FIG. 1, the first flow regulator 24 is configured to keep fluid movement in the fluid passageway at a flow value that is greater than or equal to the unrestricted flow value. The first flow regulator may actively induce fluid movement through the passageway. One example of a suitable first flow regulator is a pump. One embodiment of such a pump includes an oscillating member that alternately draws fluid from the fluid source 32 and forces the drawn fluid through the administration tube 34. In one embodiment, the pump produces a negative pressure to draw the fluid from the upstream medical fluid container and produces a positive pressure to expel fluid to the administration tube 34. It will be appreciated that fluid movement may be induced by the first flow regulator through the use of other types of devices known in the art, such as a peristaltic pump. Preferably, the first flow regulator allows fluid movement at the unrestricted flow value when it is not actively inducing fluid movement.

The second flow regulator 26 is configured to keep fluid movement in the fluid passageway 22 at a flow value less than or equal to the unrestricted flow value. Preferably, the second flow regulator functions as a flow restrictor capable of maintaining the flow value less than or equal to the unrestricted flow rate without the continuous or cyclical consumption of power. The second flow regulator may reduce fluid movement by introducing an obstruction in the fluid passageway, and may increase fluid movement by withdrawing the obstruction. One example of a suitable second flow regulator is an adjustable valve having a moveable valve member that extends into the internal volume of the fluid passageway or pinches a resilient portion of the fluid passageway. It will be appreciated that fluid movement may be reduced or increased by the second flow regulator through the use of other types of devices known in the art, such as a butterfly valve.

In the illustrated embodiment of FIG. 1, the first flow regulator 24, the second flow regulator 26, and the flow detector 28 are arranged sequentially along the fluid passageway 22, with the first flow regulator 24 disposed closest the fluid source 32. It will be appreciated that the sequential order of these elements may be changed.

Figure 2:
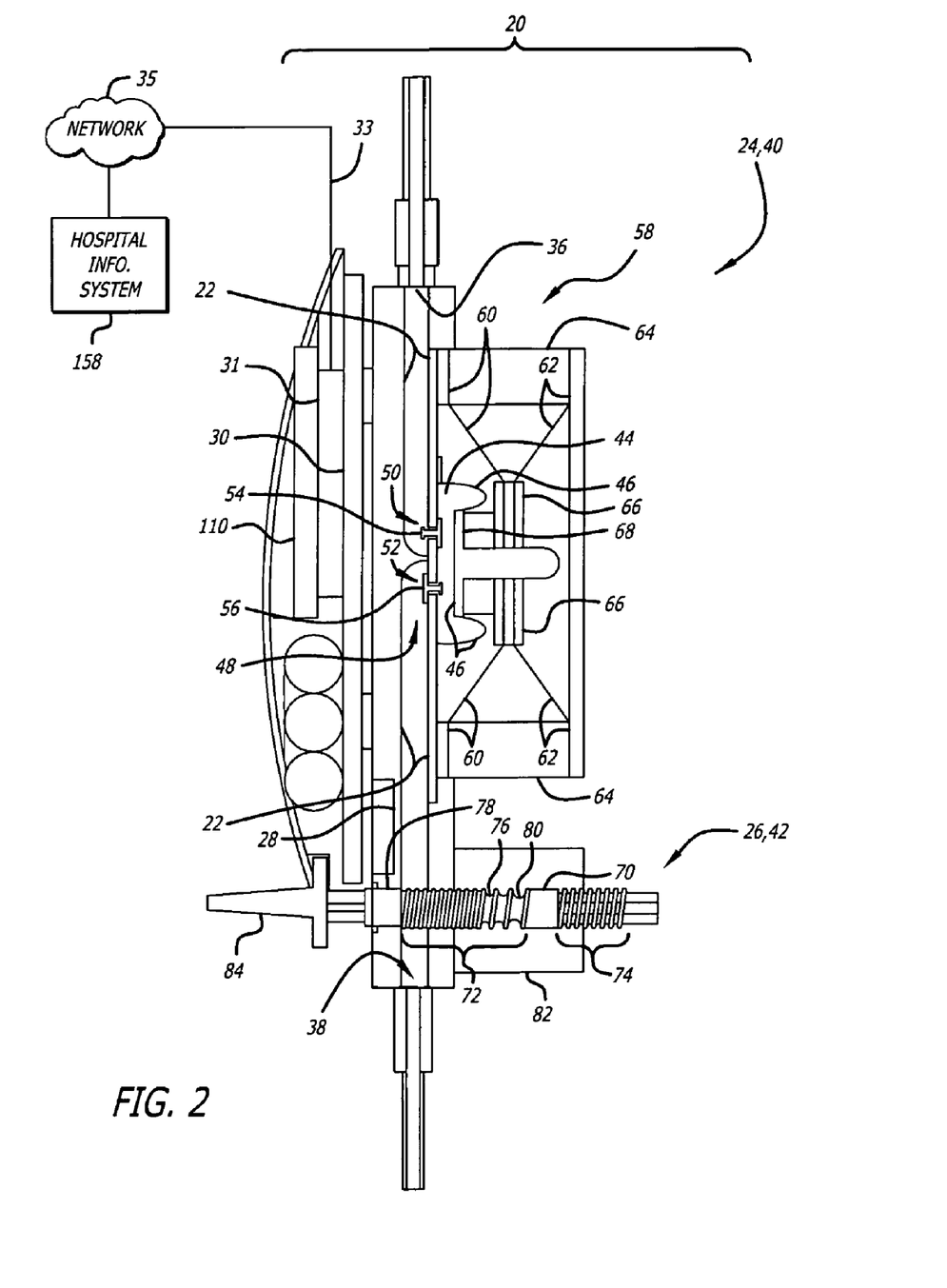
FIG. 2 is a cross-sectional side view of another system for controlling the administration of fluid showing a fluid passageway to which is connected a pump, a variably adjustable valve, a flow detector, a controller, a knob, a display, and a power source, wherein the pump comprises a pump chamber in the fluid passageway and a moveable wall adjacent the pump chamber, the moveable wall in contact with a plate coupled to a clamp of a pump driver, the pump chamber having two holes in which are located floating members of a first and a second check valve.

In FIG. 2 there is shown a cross-section of an embodiment of another system 20. A fluid passageway 22 extends longitudinally from a primary fluid inlet 36 to a primary fluid outlet 38. Adjacent and downstream from the primary fluid inlet is a first flow regulator 24, in this case a pump 40. Adjacent and upstream to the primary fluid outlet is a second flow regulator 26 that comprises a variably adjustable valve 42 in this case. A flow detector 28 is disposed between the pump and the variably adjustable valve.

The pump 40 includes a pump chamber 44 in the fluid passageway 22 and is, thus, in fluid communication with the primary fluid inlet 36. The pump chamber includes a moveable wall 46 and a pump outlet 48. The pump chamber also includes a first check valve 50 arranged to ensure one-way fluid flow from the primary fluid inlet to the pump chamber, and a second check valve 52 arranged to ensure one-way fluid flow from the pump chamber to the pump outlet. The first and second check valves are disposed sequentially within the internal volume of the fluid passageway, with the first check valve disposed closest to the primary fluid inlet.

The first and second check valves 50, 52 include a first floating member 54 and a second floating member 56, respectively. The first and second floating members are sized and shaped to move freely within respective holes in a wall of the pump chamber 44. The first floating member is arranged such that it moves to an open position when fluid pressure in the pump chamber is lower than fluid pressure in the primary fluid inlet 36. The second floating member is arranged such that it moves to an open position when fluid pressure in the pump chamber is greater than fluid pressure in the pump outlet 48. Although the check valves of the illustrated embodiment includes T-shaped floating members, it will be appreciated that one-way fluid flow may be achieved with other types of check valves known in the art, such as ball-type valves. In any case, the check valves are preferably configured to allow fluid movement at the unrestricted flow value when the pump 40 is not actively inducing fluid movement.

Still referring to FIG. 2, the moveable wall 46 of the pump chamber 44 is physically coupled to a pump driver 58. The pump driver 58 comprises a first diaphragm 60 and a second diaphragm 62 that are spatially separated by a driver housing 64. The housing keeps edges of the first and second diaphragms from moving. The first and second diaphragms have middle portions that are coupled together by a clamp 66. The clamp pulls the middle portions together such that the first and second diaphragms exert a biasing force on each other, such that movement of either one of the diaphragms is resisted by the other diaphragm. The clamp is connected to a plate 68 in contact with the moveable wall 46 of the pump chamber 44.

As shown schematically in FIG. 2, the controller 30 may be connected to a wireless communication device 31, which would communicate with a wireless network 33 via radio frequencies 35 or other wireless means known in the art. The network may be part of an existing hospital information system (OM) 158. The wireless communication device allows a set of drug delivery data to be downloaded or received from the network to the system 20. Such received data includes, but is not limited to, safety limits for checking drug delivery parameters subsequently entered into the system and an infusion program comprising several drug delivery parameters. The wireless communication device also allows another set of drug delivery data to be uploaded or transmitted from the system to the network. Without limitation, such transmitted data includes infusion status indicating the progress of drug delivery, alarm information indicating a problem or potential problem with drug delivery, and drug delivery information used for an electronic medical administration record (eMAR), such as a drug identification, drug delivery start and completion times, a drug delivery flow rate, and other information.

Figure 3:
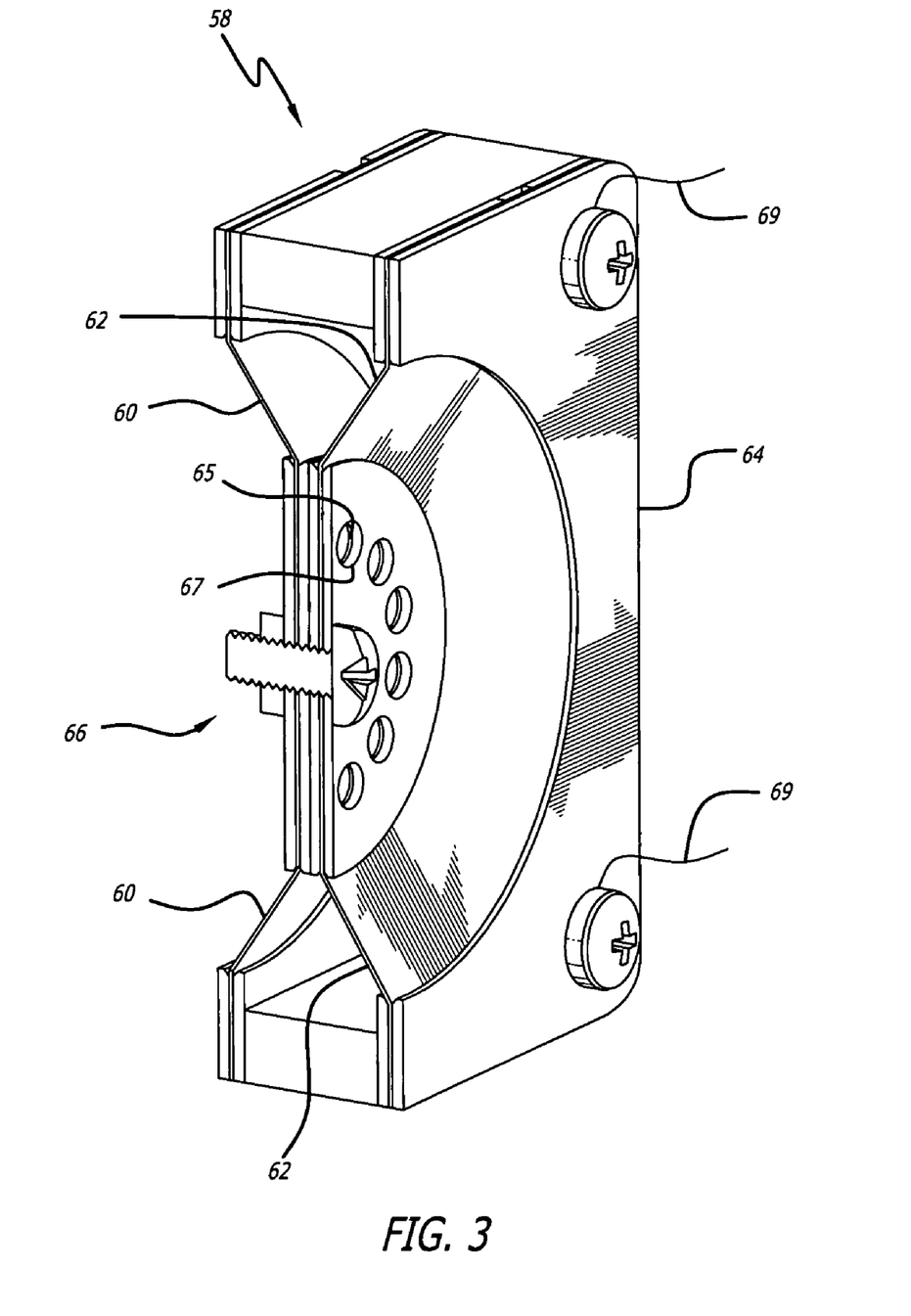
FIG. 3 is a perspective cross-sectional view of the pump driver of FIG. 2 showing a first and second diaphragm having edges and middle portions, the edges spatially separated by a housing and the middle portions held in closer proximity to each other by the clamp.

In FIG. 3 there is shown a perspective cross-sectional view of the pump driver 58 of FIG. 2. The middle portions of the first and second diaphragms 60, 62 have holes, one of which is indicated by numeral 65, which align with holes in the clamp 66, one of which is indicated by numeral 67. The holes allow air pressure on each side of the clamp to equalize while the clamp moves back and forth. A nut and bolt holds portions of the clamp together. The bolt is connected to the plate 68 (FIG. 2).

Figure 4:
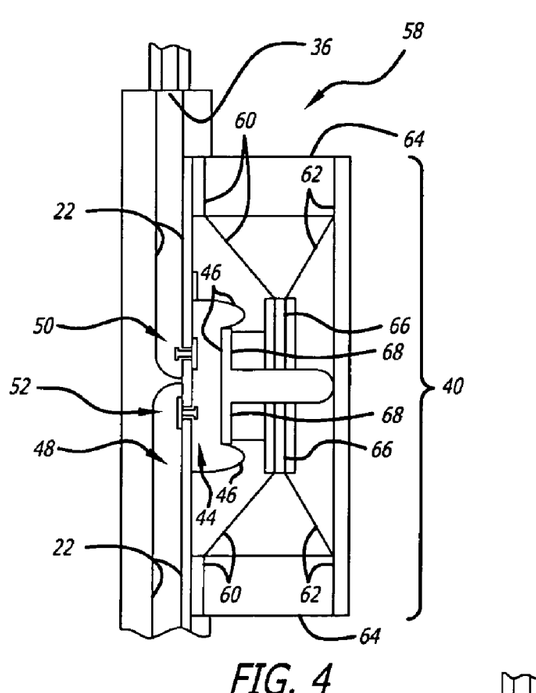
FIG. 4 is a cross-sectional detail view of the pump driver of FIG. 2 showing the first diaphragm expanded such that the clamp, the plate, and the moveable wall of the pump chamber are displaced in a first direction so as to increase the pump chamber in volume and draw fluid into the pump chamber through the first check valve.
Figure 5:
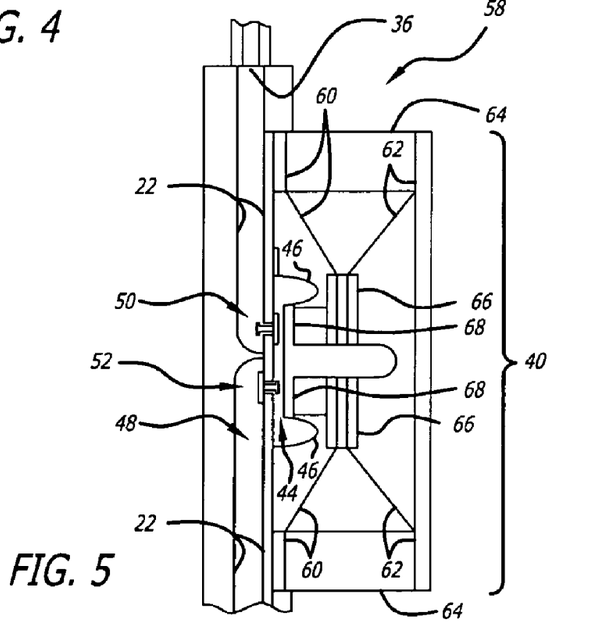
FIG. 5 is a cross-sectional detail view of the pump driver of FIG. 2 showing the second diaphragm expanded such that the clamp, the plate, and the moveable wall of the pump chamber are displaced in a second direction so as to decrease the pump chamber in volume and expel fluid out of the pump chamber through the second check valve.

Referring to FIGS. 4 and 5, the pump 40 regulates fluid movement in the fluid passageway 22 when the pump driver 58 moves the moveable wall 46 to alternatively increase and decrease the volume of the pump chamber 44. When the pump chamber volume is decreased (from FIG. 4 to FIG. 5), fluid pressure in the pump chamber increases relative to fluid pressures at the primary fluid inlet 36 and the pump outlet 48. The pressure increase causes the first check valve 50 to close and the second check valve 52 to open, thereby expelling fluid from the pump chamber to the pump outlet. Subsequently, when the pump chamber volume is increased (from FIG. 5 to FIG. 4), fluid pressure in the pump chamber decreases relative to fluid pressures at the primary fluid inlet and the pump outlet. The pressure decrease causes the second check valve to close and the first check valve to open, thereby drawing fluid from the primary fluid inlet to the pump chamber.

Referring to FIGS. 2-5, the first diaphragm 60 comprises an electroactive polymer in the form of an elastomeric dielectric polymer film in this embodiment. The film has a first side and a second side. The surface of the first side is coated with a first expandable conductive film electrically connected to a first electrode (not shown). The surface of the second side is coated with a second expandable conductive film electrically connected to a second electrode. The first and second electrodes are coupled to electrode posts, which are connected to wires 69 (FIG. 3) coupled to a voltage source. When a voltage is applied to the first and second electrodes, a pressure is created upon the dielectric film, causing the film to become thinner and to spread outward. By spreading outward, the first diaphragm moves the clamp 66 away from the moveable wall 46 of the pump chamber 44. When the applied voltage is removed, the film returns to its original shape, causing the clamp to move to its previous position with the aid of a biasing force from the second diaphragm 62. In this way, fluid movement in the fluid passageway is regulated by the pump with cyclical application and removal of power to the first diaphragm. Advantageously, power is conserved because power is not consumed continuously by the pump.

In another embodiment, the second diaphragm 62 is similar to the first diaphragm 60 in that it too has an elastomeric dielectric polymer film disposed between a pair of expandable conductive coatings. However, the second diaphragm is arranged such that when a voltage is applied to the pair of expandable conductive coatings of the second diaphragm, the dielectric polymer film spreads outward, moving the clamp 66 toward the moveable wall 46 of the pump chamber 44. When the applied voltage is removed, the dielectric polymer film returns to its original shape, causing the clamp to move to its previous position with the aid of a biasing force from the first diaphragm. Thus, fluid movement in the fluid passageway is regulated by the pump of this embodiment with cyclical power supplied to the first diaphragm out of phase with cyclical power supplied to the second diaphragm. With this arrangement, there is greater displacement of the moveable wall and thus, greater fluid movement relative to powering the first diaphragm alone.

In an alternative embodiment not shown, the pump driver comprises a piezoelectric device coupled to the moveable wall 46 of the pump chamber 44. The piezoelectric device is configured to move the moveable wall in response to a voltage applied to the device. Piezoelectric devices used for pumping fluids are well known in the art and, thus, require no further description here.

Referring again to FIG. 2, the variably adjustable valve 42 includes a cylindrical valve member 70 extending across the fluid passageway 22. The variably adjustable valve 42 regulates fluid movement in the fluid passageway based on the position of the valve member, which has a fluid contacting portion 72 and a threaded portion 74. The fluid contacting portion has an outer surface with a groove 76 extending in a helical manner around and along a length of the valve member. The groove has a width and a depth that varies along the length of the groove. Near one end of the groove, the groove has a maximum width and a maximum depth. The width and the depth decrease toward an opposite end of the groove. Fluid is completely blocked when the valve member is positioned such that fluid contacts a section 78 of the fluid contacting portion having no groove. Fluid movement corresponding to the unrestricted flow value may occur when the valve member is positioned such that fluid passes through a section 80 of the fluid contacting portion in which the groove has the maximum width and the maximum depth.

The position of the cylindrical valve member 70 is controlled by a restrictor driver 82 coupled to the threaded portion of the valve member. Not shown are a motor and a gear in the restrictor driver, which adjusts the position of the valve member when power is applied to the motor. The position of the valve member may also be controlled by a knob 84 which is sized and shaped to allow a user of the system 20 to manually adjust fluid movement. The knob functions as a user input device, allowing the user to adjust fluid movement in the fluid passageway to a desired or target flow value. In one embodiment, the knob is coupled directly to the valve member so that rotation of the knob results in a corresponding movement of the valve member. In another embodiment, the knob is coupled to the controller 30, described further below, such that rotation of the knob results in a change in power supplied to the motor of the pump driver or a change in the power supplied to the pump driver.

Figure 6:
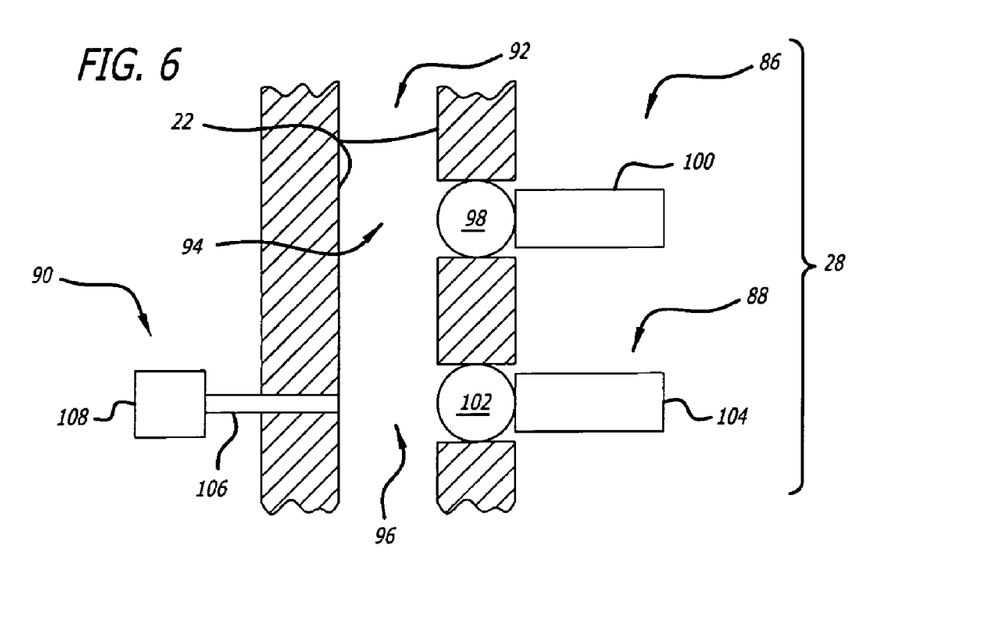
FIG. 6 is a cross-sectional detail view of the flow detector of FIG. 2 showing a heat source, a light source, and a light detector, each of which is disposed outside an internal volume of the fluid passageway, wherein the heat source comprises a first laser device that heats fluid in a heating region in the fluid passageway, the light source comprises a second laser device directed toward fluid in an interrogating region in the fluid passageway, and the light detector comprises a photodiode in optical communication with the fluid in the interrogating region.

In FIG. 6 there is shown a flow detector 28 configured to produce and detect a thermal change in fluid in the fluid passageway 22 and to provide a detector signal representative of an existing fluid flow value in the fluid passageway. The flow detector 28 comprises a heat source 86, a light source 88, and a light detector 90, each of which are disposed outside an internal volume 92 of the fluid passageway 22. The heat source is disposed closest the pump outlet 48 (FIG. 2) and upstream from the light source. The heat source is adapted to heat fluid located at a heating region 94 in the fluid passageway. The light source is adapted to produce an interrogating light directed toward fluid located at an interrogating region 96 in the fluid passageway. The light detector is adapted to provide a detector signal representative of fluid movement.

In the illustrated embodiment, the heat source 86 is an optical device that comprises an first optical lens 98 disposed on a wall of the fluid passageway 22 and a first laser device 100 in optical contact with the first optical lens. The first laser device produces an amplified beam of light that is directed by the first optical lens 98 to the heating region 94 in the fluid passageway. The light has a wavelength and energy level selected to heat fluid in the heating region 94, thereby producing a thermal change or marker in a portion of a fluid stream traveling through the fluid passageway. It will be appreciated that other types of heat sources, including non-optical devices, may be employed to produce the thermal marker.

Still referring to FIG. 6, the light source 88 comprises an second optical lens 102 disposed on a wall of the fluid passageway 22 and a second laser device 104 in optical contact with the second optical lens. The second laser device produces an interrogating light that is directed by the second optical lens 102 to the interrogating region 96 in the fluid passageway. The interrogating light has a wavelength and energy level selected so as to prevent or minimize heating of fluid in the interrogating region.

The light detector 90 comprises an optical waveguide 106 disposed on a wall of the fluid passageway 22 and a photodiode 108 in optical contact with the waveguide. The photodiode is adapted to detect optical characteristics of the fluid in the interrogating region 96, and to detect changes in the optical characteristics when the heated fluid from the heating region 94 enters the interrogating region. With this arrangement, a detector signal produced by the light detector may represent a time period in which the thermal change travels a predetermined distance that separates the heating region and the interrogating region. The predetermined distance corresponds to a predetermined volume of a portion of the fluid passageway. Thus, it will be appreciated that the flow detector 28 provides a direct and non-invasive measurement of flow rate in terms of volume per time period.

Referring again to FIG. 2, a controller 30 is in communication with the pump driver 58, the restrictor driver 82, and the flow detector 28. The controller is also in communication with a display screen 110, which may be used to indicate an existing flow value of fluid movement in the fluid passageway 22. As discussed in greater detail below, the controller receives a detector signal from the flow detector 28. Based on the detector signal, the controller produces to a pump signal and a restrictor signal to adjust the existing flow value to a desired or target flow value, and to automatically maintain the existing flow value at the target flow value. The pump signal results in the application and removal of power to electrically activated elements of the pump driver, such as the first diaphragm 60 or a piezoelectric device. The restrictor signal results in the application and removal of power to the motor of the pump driver.

Figure 7:
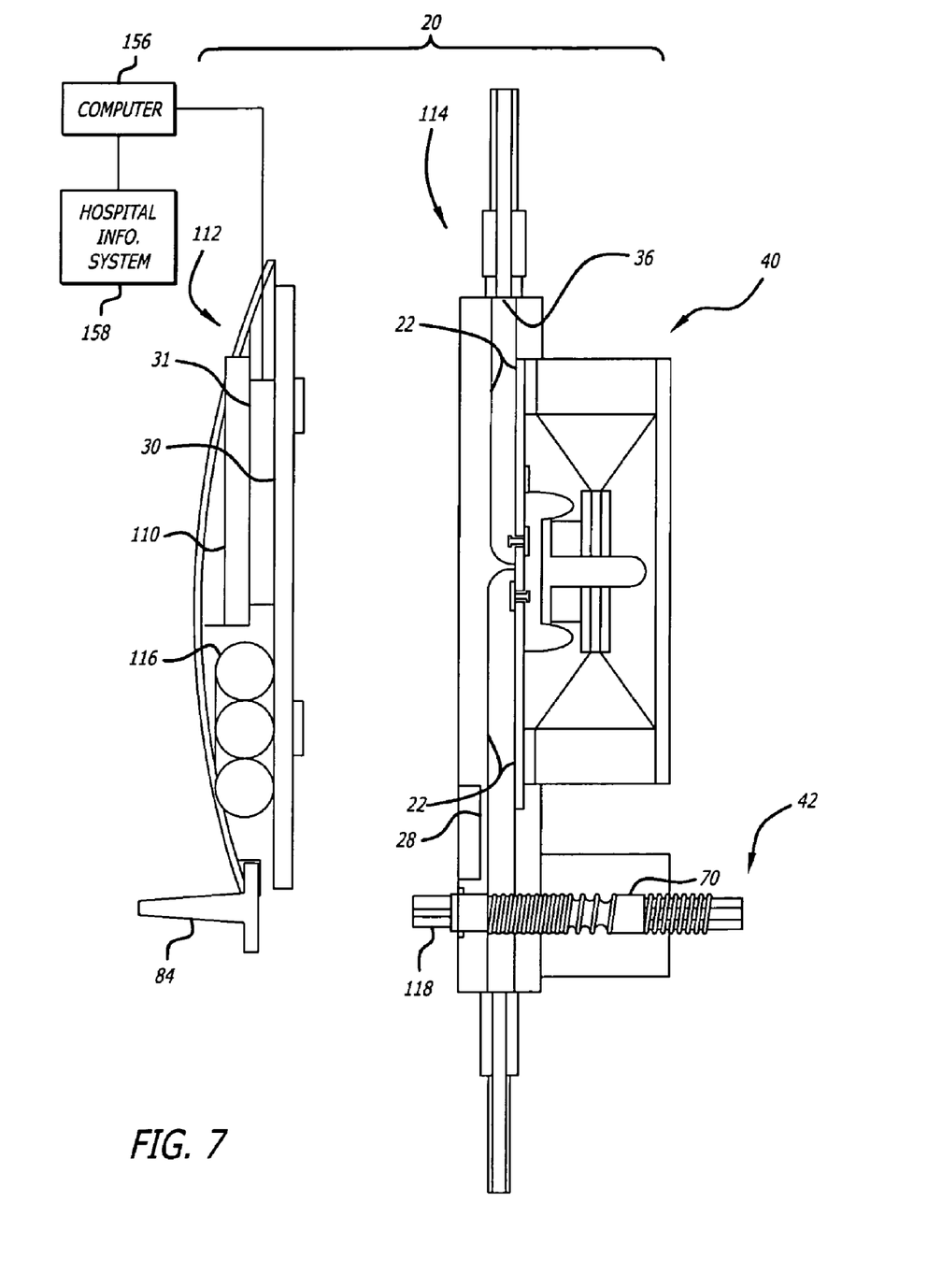
FIG. 7 is a cross-sectional side view of another system for controlling administration of fluid showing a reusable assembly detached from a disposable assembly, wherein the reusable assembly comprises a display, a power source, a knob, and a controller, and the disposable assembly comprises a fluid passageway to which is attached a pump, a flow detector, and a variably adjustable valve.

In FIG. 7 there is shown another embodiment of a system 20 in accordance with the present invention. The system comprises a reusable assembly 112 and a disposable assembly 114. The reusable and disposable assemblies are configured to be removably connected to each other. The assemblies are shown detached from each other. Not shown is a means for connecting the assemblies that includes an electrical connector and mechanical connector. The electrical and mechanical connectors may be combined in an electromechanical connector. It will be appreciated that electrical, mechanical, and electromechanical connectors are well known in the art and, thus, require no further description here.

In use, the fluid contacting elements of the system 20 are discarded after administration of medical fluid to a patient is completed. Elements of the system that are not contaminated by the medical fluid are retained for future use in order to reduce medical costs. In the illustrated embodiment, the disposable assembly 114 includes the fluid passageway 22, the pump 40, the variably adjustable valve 42, the flow detector 28, and a manual adjustment device 118 in the form of a small knob sized to be manipulated by a user. The small knob is connected to the valve member 70 and allows the user to adjust the existing flow value manually after the reusable assembly has been detached. The reusable assembly 112 includes the controller 30, the display 110, the knob 84, and a power source 116. In this case, the power source comprises a plurality of load cells, which supply power to electrical devices on both the reusable and disposable assemblies. Thus, when the reusable assembly is detached, the pump and the variably adjustable valve lose power. Even without power, fluid movement up to the unrestricted flow value is possible.

Figure 8:
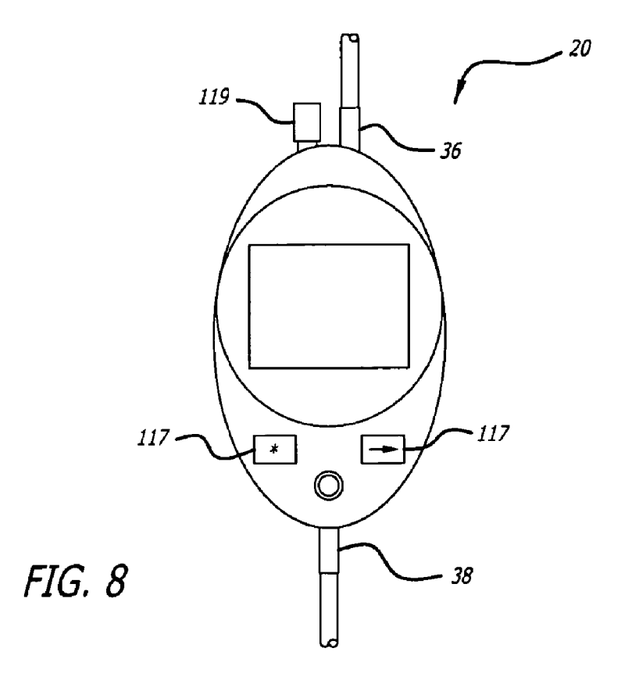
FIG. 8 is a front view of yet another system showing a primary fluid inlet in fluid communication with a secondary fluid inlet.

Referring next to FIG. 8 showing a further embodiment in accordance with the present invention, a system 20 includes a primary fluid inlet 36 and a secondary fluid inlet 119. Although not shown, the primary fluid inlet and the secondary fluid inlet lead to a Y-shaped conduit that is part of the fluid passageway 22. With this arrangement, fluids from the primary and secondary fluid inlets are simultaneously drawn into the pump chamber 44. User input buttons 117 are provided to allow a user to respond to information shown on the display 110.

Figure 9:
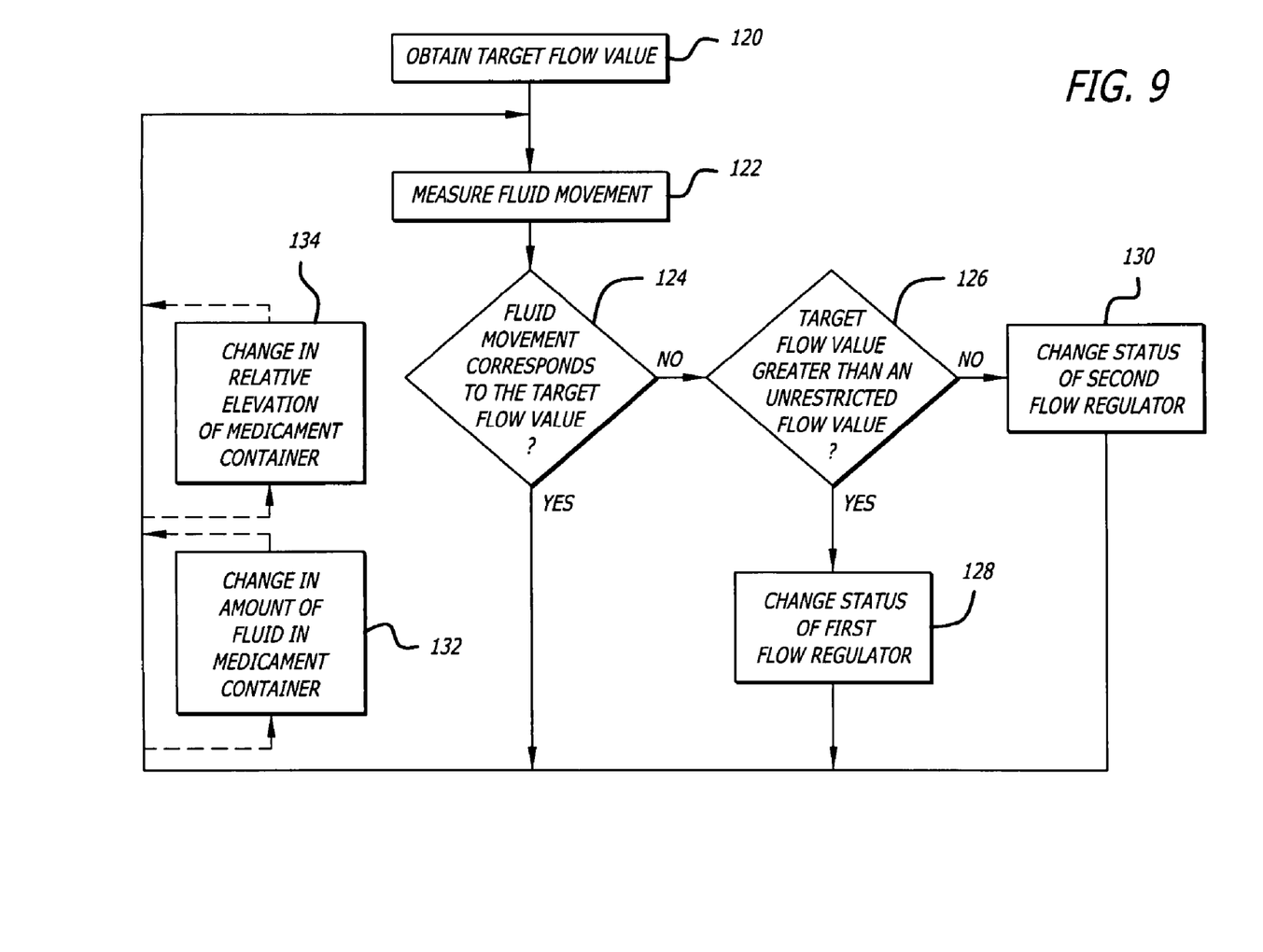
FIG. 9 is a flow diagram of a method of controlling the delivery of fluid showing automatically changing the operational status of a first and a second flow regulator based on a comparison of a target flow value to a measurement of fluid movement and to an unrestricted flow value, the operational status changes also being made automatically in response to changes in the amount of fluid in a fluid source and changes in the relative elevation of the fluid source.

Turning now to FIG. 9 in which is shown an embodiment of a method in accordance with aspects of the invention. Although the method will be described in terms of the systems of FIGS. 1, 2 and 7, it will be appreciated that other systems may be used to implement the method. A target flow value is obtained 120 when a user manipulates a user input device. Fluid movement is measured 122 in the fluid passageway by a flow detector, which supplies a detector signal to a controller. The controller determines 124, based at least on the detector signal, whether the measured fluid movement is substantially equivalent to or corresponds to the target flow value. If yes, no change is made to the operational status of a first flow regulator, such as a pump, or to the operational status of a second flow regulator, such as a variably adjustable valve. The process is then repeated beginning with another measurement 122 of fluid movement.

Still referring to FIG. 9, if at 124 the measured fluid movement does not correspond to the target flow value, the controller determines 126 whether the target value is greater than an unrestricted flow value. If yes, a change 128 is made to the operational status of the first flow regulator. This change in operational status may, for example, involve the controller producing a pump signal that incrementally increases or decreases power supplied to a pump driver. If at 126 the target value is less than or equal to the unrestricted flow value, a change 130 is made to the operational status of the second flow regulator. This change in operational status may, for example, involve the controller producing a restrictor signal that actuates a restrictor driver in order to move a valve member in an incrementally more open or more closed position. The process of making an incremental change to the operational status of the first flow regulator or the second flow regulator is repeated beginning with another measurement 122 of fluid movement until the fluid movement corresponds to the target flow value.

By repeating the process with another measurement 122 of fluid, it will be appreciated that the system 20 is configured to adjust the existing flow value when the existing flow value strays from the target value for any reason. For example, a change 132 in the amount of fluid in a medicament container may cause the existing flow value to decrease. Such a change in the amount of fluid may occur during the normal course of administration of fluid to a patient or when a near empty medicament container is replaced with a full medicament container. Also, a change 134 in elevation of the medicament container relative to an outlet of an administration tube may cause the existing flow value to stray from the target value.

The change in relative elevation of the medicament container may occur may when a patient is being moved in such a way that the medicament container is lowered toward the patient, which may result in a decrease in pressure head at the administration tube outlet connected to the patient and, thus, a decrease in fluid movement. The change in elevation may also occur when a patient stands up from a sitting position, which may result in an increase in pressure head at the administration tube outlet and, thus, an increase in fluid movement. In any event, a change will be made by the controller to the operational status of the first flow regulator or the second flow regulator in order to maintain the existing flow value at the target flow value.

Figure 10:
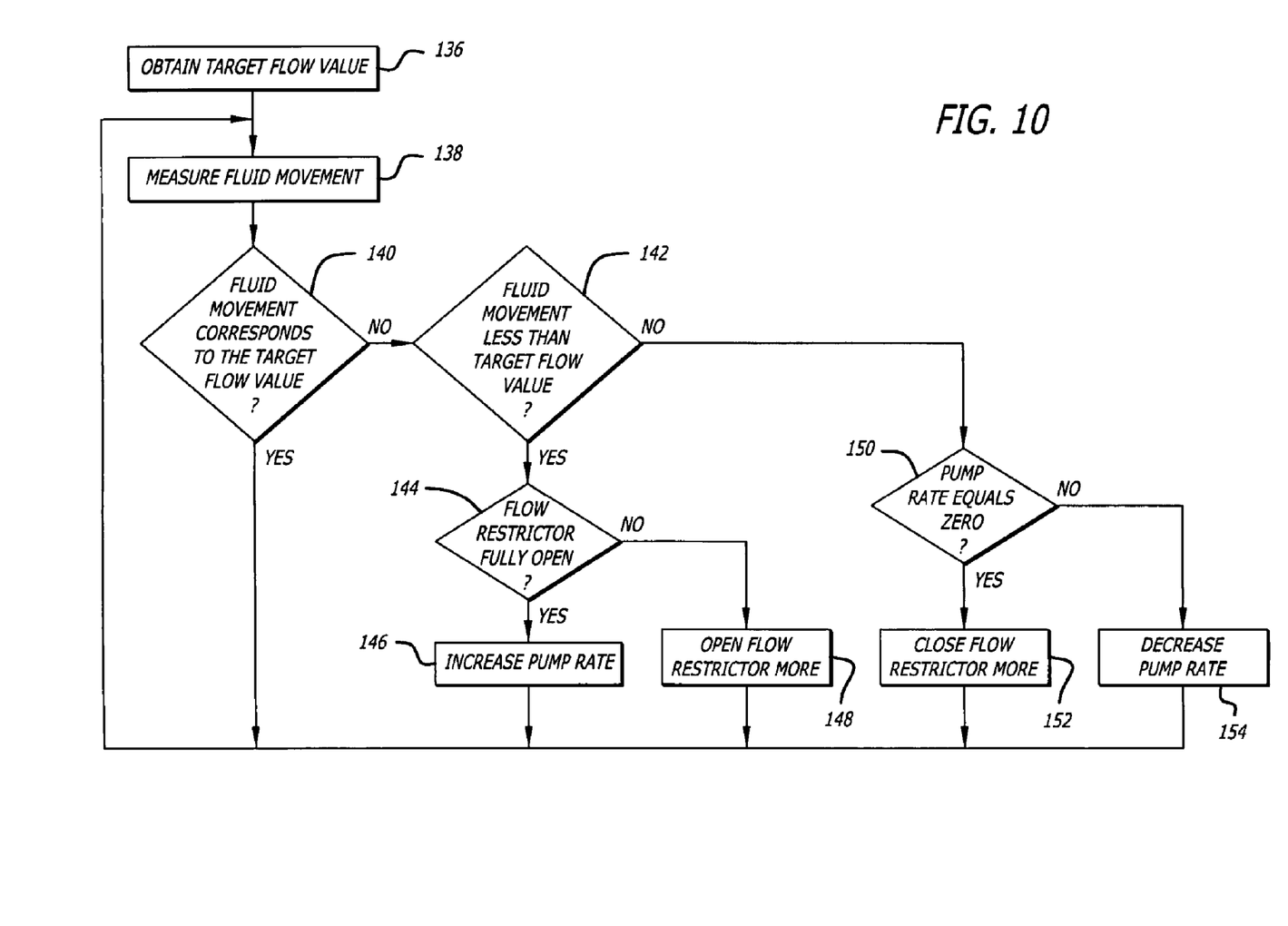
FIG. 10 is a flow diagram of another method of controlling administration of fluid showing comparing a target flow value to a measurement of fluid movement, comparing a target flow value to the unrestricted flow value, determining the operational status of a first and a second flow regulator, and, based on a result of the determination, incrementally changing pumping activity in a first flow regulator or incrementally moving a second flow regulator to a more open or more closed position.

Referring now to FIG. 10, there is shown another method in accordance with aspects of the invention wherein the unrestricted flow value is not be predetermined. A target flow value is obtained 136 and fluid movement is measured 138. The controller then determines 140 whether the measured fluid movement is substantially equal to or corresponds to the target flow value. If yes, no change is made to the operational status of the first flow regulator or the second flow regulator, and the process is repeated beginning with another measurement 136 of fluid movement.

If at 140 the measured fluid movement does not correspond to the target flow value, the controller determines 142 whether the fluid movement is less than the target value. If yes, the controller determines 144 whether the second flow regulator is at a fully open position. If yes, the controller infers that the target flow value is greater than the unrestricted flow value and instructs the first flow regulator in incrementally increase 146 pumping slightly. This process of increasing pumping activity incrementally is repeated until the fluid movement corresponds to the target flow value.

If instead at 144 the first flow regulator is not in a fully open position, controller assumes that the target flow value is less than or equal to the unrestricted flow value and instructs the second flow regulator to incrementally move 148 to a slightly more open position. This process of moving the second flow regulator incrementally to a more open position is repeated until a fully open position is reached or the fluid movement corresponds to the target flow value, whichever occurs first. When a fully open position is reached first, the controller infers that the target flow value is greater than the unrestricted flow value and instructs the first flow regulator to incrementally increase 146 pumping activity slightly. This process of increasing pumping activity incrementally is repeated until the fluid movement corresponds to the target flow value.

Still referring to FIG. 10, when instead at 142, the fluid movement is greater than the target value, the controller determines 150 whether the first flow regulator 24 is inactive such that, for example, pumping activity is at zero. If yes, the controller 30 infers that the target flow value is less than or equal to the unrestricted flow value and instructs the second flow regulator 26 to incrementally move 152 to a slightly more closed position. This process of moving the second flow regulator incrementally to a more closed position is repeated until the fluid movement corresponds to the target flow value.

If at 150, the first flow regulator is active such that, for example, pumping activity is non-zero, the controller assumes that the target flow value is greater than the unrestricted flow value and instructs the first flow regulator to incrementally decrease 154 pumping activity slightly. This process of decreasing pumping activity incrementally is repeated until pumping activity reaches zero or the fluid movement corresponds to the target flow value, whichever occurs first. When pumping activity reaches zero first, controller infers that the target flow value is less than the unrestricted flow value and instructs the second flow regulator to incrementally move 152 to a slightly more closed position. This process of moving the second flow regulator incrementally to a more closed position is repeated until the fluid movement corresponds to the target flow value.

In a further embodiment, the reusable assembly 112 (FIG. 7) includes a bi-directional communication device 31 for communicating data via wired or wireless means with a computer 156 shown symbolically in block form. The communication device may be a detachable module electromechanically connected to the controller or it may be an integral part of the reusable assembly. The computer provides the controller 30 with drug delivery data from a hospital information system 158, shown symbolically in block form, to assist the user in administering the right drug to the right patient at the right dose and via the right administration route. Such data received by the reusable assembly may include a drug name and a prescribed infusion rate. Data transmitted from the reusable assembly to the computer may include a target flow value programmed into the reusable assembly by a user and measurements of fluid movement taken during the course of infusion. In this way, an alert may be shown on the display 110 of the reusable assembly, or elsewhere on the hospital information system, when the target flow value entered by the user does not correspond to the prescribed infusion rate. With the communication device, medical records kept by the hospital information system may be automatically updated continuously or periodically during the course of infusion.

While several particular forms of the invention have been illustrated and described, it will also be apparent that various modifications can be made without departing from the scope of the invention. It is also contemplated that various combinations or subcombinations of the specific features and aspects of the disclosed embodiments can be combined with or substituted for one another in order to form varying modes of the invention. Accordingly, it is not intended that the invention be limited, except as by the appended claims.

I claim:

1. A fluid control system for controlling administration of fluid from a medicament container, the system comprising:
   a fluid passageway comprising an inlet, an outlet, and an internal volume through which unrestricted movement of fluid corresponds to an unrestricted flow value;
   a first flow regulator attached to the fluid passageway between the inlet and the outlet and configured to keep fluid movement in the fluid passageway at a flow value greater than or equal to the unrestricted flow value;
   a second flow regulator attached to the fluid passageway between the first flow regulator and the outlet and configured to keep the fluid movement in the fluid passageway at a flow value less than or equal to the unrestricted flow value;
   a flow detector attached to the fluid passageway between the first flow regulator and the second flow regulator and configured to take a measurement of the fluid movement in the fluid passageway; and
   a controller removably attached to the fluid passageway and coupled to the flow detector, the first flow regulator, and the second flow regulator, the controller configured to control the first and second flow regulators in response to the measurement by the flow detector.

2. The system of claim 1 wherein the first flow regulator comprises a pump chamber having a moveable wall coupled to a pump driver, the pump chamber disposed in the fluid passageway and configured for one-way fluid flow in a direction from the inlet to the outlet of the fluid passageway, the pump driver comprising an elastomeric dielectric film having a first side and a second side, the first side coated with a first expandable conductive film connected to a first electrode, the second side coated with a second expandable conductive film connected to a second electrode, the dielectric film configured to expand in response to a voltage applied to the first and second electrodes.

3. The system of claim 1 wherein the second flow regulator is further configured to keep the fluid movement in the fluid passageway at a flow value equal to the unrestricted flow value.

4. The system of claim 1 wherein the second flow regulator comprises a variably adjustable valve configured to restrict the fluid movement in the fluid passageway.

5. The system of claim 1 wherein the flow detector comprises:
   a heat source disposed outside the internal volume of the fluid passageway and adapted to heat fluid located at a heating region in the fluid passageway;
   a light source disposed outside the internal volume of the fluid passageway and adapted to produce an interrogating light directed toward fluid located at an interrogating region in the fluid passageway;
   a light detector disposed outside the internal volume of the fluid passageway and adapted to detect optical characteristics of the fluid in the interrogating region, and to detect changes in the optical characteristics when the heated fluid from the heating region enters the interrogating region.

6. The system of claim 1 further comprising a wireless communication device adapted for bi-directional communication with a wireless network, the communication device connected to the controller and configured to receive a first set of drug delivery data from the network and to transmit a second set of drug delivery data to the network.

7. The system of claim 1 wherein the first flow regulator comprises:
   a pump chamber, the pump chamber disposed in the fluid passageway and configured for one-way fluid flow in a direction from the inlet to the outlet of the fluid passageway;
   a moveable wall;
   a pump driver coupled to the moveable wall, the pump driver comprising a first diaphragm and a second diaphragm, the first diaphragm and the second diaphragm coupled together by a clamp such that the first and second diaphragms exert a biasing force on the other, the first diaphragm configured to expand and move the clamp away from the moveable wall in response to a first applied voltage, the second diaphragm configured to expand and move the clamp towards the moveable wall in response to a second applied voltage.

8. The system of claim 7, wherein the first diaphragm comprises a first elastomeric dielectric film having a first side and a second side, the first side of the first elastomeric dielectric film coated with a first expandable conductive film connected to a first electrode, the second side of the first elastomeric dielectric film coated with a second expandable conductive film connected to a second electrode, and wherein the second diaphragm comprises a second elastomeric dielectric film having a first side and a second side, the first side of the second elastomeric dielectric film coated with a third expandable conductive film connected to a third electrode, the second side of the second elastomeric dielectric film coated with a fourth expandable conductive film connected to a fourth electrode.

9. The system of claim 7, wherein the pump chamber includes a first check valve configured to allow the fluid movement into the pump chamber and a second check valve configured to allow the fluid movement out of the pump chamber.

10. The system of claim 7, wherein moving the clamp away from the moveable wall increases a volume of the pump chamber, and moving the clamp towards the moveable wall decreases the volume of the pump chamber.

11. A method of controlling administration of fluid from a medicament container, the method comprising:
obtaining a target flow value;
moving fluid through a disposable assembly comprising a fluid passageway and a flow regulating apparatus, the fluid passageway comprising an inlet, an outlet, and an internal volume through which unrestricted movement of the fluid corresponds to an unrestricted flow value, the flow regulating apparatus comprising a first flow regulator and a second flow regulator, the flow regulating apparatus between the inlet and the outlet;
taking a measurement of fluid movement in the fluid passageway; and
actuating the flow regulating apparatus when the fluid movement does not correspond to the target flow value, including changing the operational status of the second flow regulator when the target flow value is less than the unrestricted flow value, and changing the operational status of the first flow regulator when the target flow value is greater than the unrestricted flow value.

12. The method of claim 11 wherein actuating the flow regulating apparatus, includes changing the operational status of the second flow regulator when the target flow value is equal to the unrestricted flow value.

13. The method of claim 11 wherein actuating the flow regulating apparatus comprises actuating the flow regulating apparatus when there is a change in the amount of fluid in the medicament container or a change in elevation of the medicament container relative to an outlet of an administration tube extending from the outlet of the fluid passageway.

14. The method of claim 11 wherein actuating the flow regulating apparatus comprises applying a voltage to a first electrode and a second electrode, the first electrode connected to a first expandable conductive coating on a first side of an elastomeric dielectric film, the second electrode connected to a second expandable conductive coating on a second side of the elastomeric dielectric film, the elastomeric dielectric film coupled to a moveable wall disposed on the fluid passageway and configured to expand in response to the applied voltage.

15. The method of claim 11 wherein taking a measurement of fluid movement in the fluid passageway comprises:
heating fluid in a heating region in the fluid passageway, the fluid heated with a heat source disposed outside the internal volume of the fluid passageway;
illuminating fluid in an interrogating region in the fluid passageway, the fluid illuminated with a light source disposed outside the internal volume of the fluid passageway;
detecting optical characteristics of the fluid in the interrogating region, the optical characteristics detected with a light detector disposed outside the internal volume of the fluid passageway; and
detecting changes in the optical characteristics, the changes detected with the light detector.

16. The method of claim 11 wherein obtaining a target flow values comprises receiving a first set of drug delivery data from a network.

17. The method of claim 11 further comprising:
receiving a first set of drug delivery data from a network;
comparing the obtained target flow value with the first set of drug delivery data; and
transmitting a second set of drug delivery data to the network.

18. A fluid control system for controlling administration of fluid from a medicament container, the system comprising:
a fluid passageway comprising an inlet, an outlet, and an internal volume through which unrestricted movement of fluid corresponds to an unrestricted flow value;
a pump attached to the fluid passageway downstream of the inlet and configured to keep fluid movement in the fluid passageway at a flow value greater than or equal to the unrestricted flow value, the pump comprising:
a pump chamber configured for one-way fluid flow in a direction from the inlet to the outlet;
a moveable wall;
a first diaphragm coupled to the moveable wall and configured to expand to increase a volume of the pump chamber; and
a second diaphragm coupled to the moveable wall and configured to expand to decrease the volume of the pump chamber;
an adjustable valve attached to the fluid passageway downstream of the pump and configured to keep the fluid movement in the fluid passageway at a flow value less than or equal to the unrestricted flow value;
a flow detector attached to the fluid passageway between the pump and the adjustable valve and configured to take a measurement of the fluid movement in the fluid passageway; and
a controller removably attached to the fluid passageway and coupled to the flow detector, the pump, and the adjustable valve, the controller configured to control the pump and the adjustable valve in response to the measurement by the flow detector.

19. The system of claim 18, wherein the first diaphragm comprises a first elastomeric dielectric film having a first side and a second side, the first side of the first elastomeric dielectric film coated with a first expandable conductive film connected to a first electrode, the second side of the first elastomeric dielectric film coated with a second expandable conductive film connected to a second electrode, and wherein the second diaphragm comprises a second elastomeric dielectric film having a first side and a second side, the first side of the second elastomeric dielectric film coated with a third expandable conductive film connected to a third electrode, the second side of the second elastomeric dielectric film coated with a fourth expandable conductive film connected to a fourth electrode.

20. The system of claim 18, wherein the controller is configured to:
- obtain a target flow value;
- obtain, from the flow detector, a measurement of the fluid movement in the fluid passageway;
- change an operational status of the pump when the target flow value is greater than the unrestricted flow value; and
- change an operational status of the adjustable valve when the target flow value is less than the unrestricted flow value.

* * * * *